US00PP08527P

United States Patent [19]

de Ruiter

[11] Patent Number: Plant 8,527

[45] Date of Patent: Jan. 4, 1994

[54] MINIATURE ROSE PLANT NAMED RUIRUPO

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 801,528

[22] Filed: Dec. 2, 1991

[51] Int. Cl.[5] ..... A01H 5/00

[52] U.S. Cl. ..... Plt./10

[58] Field of Search ..... Plt. 10

*Primary Examiner*—Howard J. Locker

*Attorney, Agent, or Firm*—Christie, Parker & Hale

[57] ABSTRACT

A new variety of miniature rose plant having red flowers produced on a good pot forcing plant also suitable for growing outdoors in gardens.

2 Drawing Sheets

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Ruirupo'.

Among the novel characteristics possessed by this new variety which distinguishes it from its parents and all other varieties of which I am aware are its red flowers borne on a plant particularly suited for production of flowering pot plants and for growing in outdoor gardens. The new variety can be reproduced through propagation by cuttings, grafting, budding, and micropropagation. Flowers of the new variety are long lasting on the plant. Asexual reproduction by budding, grafting, and propagation of cuttings of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

One illustration is of a plant of the new variety of miniature rose showing flowering and growth habit; and The other illustration shows details of the new miniature rose variety.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, one illustration shows one sample of flowering plant of the new variety depicting the pot plant habit of growth and flowering. Since flowering is nearly continuous, this floriferous variety can remain attractively in bloom for long periods when given proper care and culture.

The other illustration shows details of the new variety. In the illustration there is shown the top of a young shoot, 1; compound three and five leaflet leaves, 2 and 3, respectively; a stem, 5; buds, 6 and 7; a flower, 8, about one-half open; and a flower 9, fully open. Also shown are flower stems 10, 11 and 12, with reproductive organs. 4 depicts the bud just prior to opening of the petals.

The following further horticultural observations were made of specimens grown under glass in Holland.

Flower

Blooming habit: Nearly continuous.

A. Bud:

(1) *Size.*—Medium.

(2) *Form.*—Ovate (before separation of sepals); urn shaped after sepals part.

(3) *Color.*—As sepals divide, bud color is near 45A.

(4) *Sepals.*—Longer than bud, simple to foliated.

(5) *Peduncle.*—Length — medium to long for miniature. Aspect — straight. Strength — erect. Color — rear 139A to B medium green.

B. Bloom:

*Flower.*—Medium size for miniature; viewed from above — irregularly rounded; viewed from side, (a) upper part of fully opened flower, flattened convex; (b) lower part of fully opened flower, flat.

(1) *Size.*—Average size when fully expanded — about 5 to 6 cm.

(2) *Borne.*—Singly, one to a stem.

(3) *Form.*—Ovoid becoming flat; outer petals reflex and quill to points; inner petals reflex and roll under.

(4) *Petalage.*—Many petaled under normal conditions — fully semi-double, about 20 petals.

(5) *Color.*—After sepals separate, near 45A; when sepals part and petals being to unfurl, color is from near to 43A to 45A; petals' top surface tends to from near to 43A to 46C; reverse surface tends to be similar to top surface. Coloring at point of petal attachment is near 2C. Overall tonality from a distance is attractive red.

(6) *Pedicel.*—Very few hairs or prickles.

(7) *Fragrance.*—Slight.

C. Petals:

(1) *Texture.*—Very good substance.

(2) *Appearance.*—Inside velvety and outside satiny.

(3) *Form and size.*—Medium for miniature, obovate.

(4) *Arrangement.*—Regularly arranged, imbricated.

(5) *Petaloids in center.*—Few to none.

(6) *Lasting quality.*—Long lasting quality on plant.

Reproductive Organs

A. Stamens, filaments and anthers:

*Arrangement and color.*—Regularly arranged around styles; color filaments — yellow.

B. Pollen:

*Color.*—Yellow orange.

C. Styles: Short, white, generally not hairy.

D. Stigmas: Positioned above anthers.

E. Hips: Very small, pear-shaped.

Plant

A. Form: Upright to bushy.

B. Growth: Vigorous, about 50 cm in height by about 35 cm in breadth.

C. Foliage: Compound 3, and 5 leaflets.

(1) *Size.*—Medium for a miniature.

(2) *Quantity.*—Abundant.

(3) *Color.*—Foliage at time of first flowering — light green, near 138B to C.

(4) *Shape.*—Oval, pointed.

(5) *Texture.*—Upper side is weak to medium glossy; underside is matte.

(6) *Edge.*—Serrate.

(7) *Serration.*—Ordinary, acuminate apices.

(8) *Leaf stem.*—Color.— medium green.

(9) *Stipules.*—Short, simple, medium green, distinct auricle.

(10) *Leaflets.*—Cross-section — slight concave, little or no undulation at margin; terminal leaflet (blade) — short, narrow, obtuse base; petiole —short.

D. Wood:

(1) *New wood.*—Color — light to medium green, near 139C to D.

(2) *Old wood.*—Color — near 139A to B.

E. Prickles (Thorns):

(1) *Prickles.*—Present, quantity (main stalk) — ordinary; On laterals from stalk — ordinary; Form —straight; Shape of upper side — flat Shape of lower side — concave to flat. Length — $\leqq 5$ mm, medium; $>5$ mm, medium. Color — tan to pale pink, depending on position on stem. Position — irregular.

I claim:

1. A new and distinct variety of rose plant of the miniature rose class, substantially as shown and described.

* * * * *

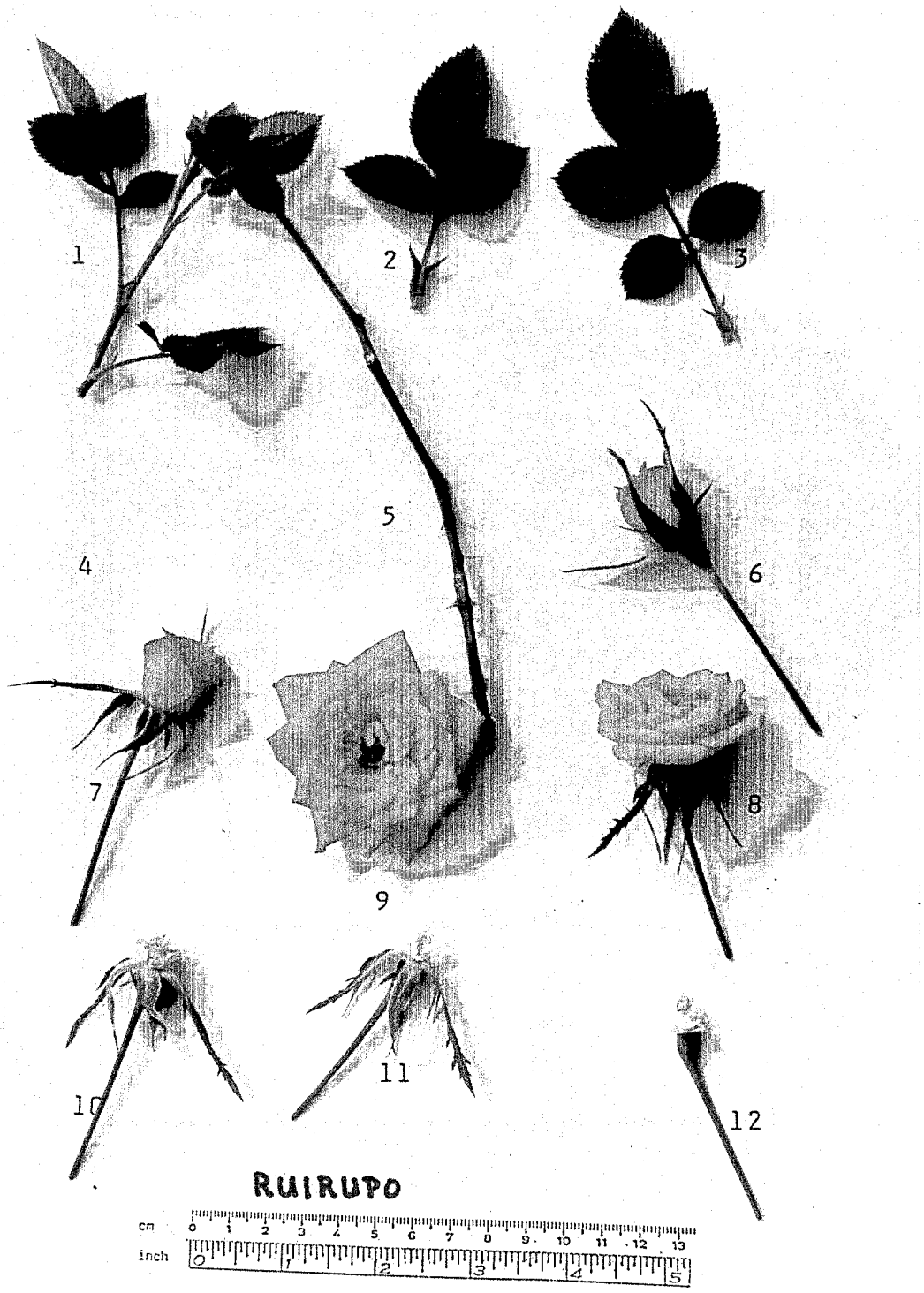
1
2
3
4
5
6
7
8
9
10
11
12
RUIRUPO
cm
inch

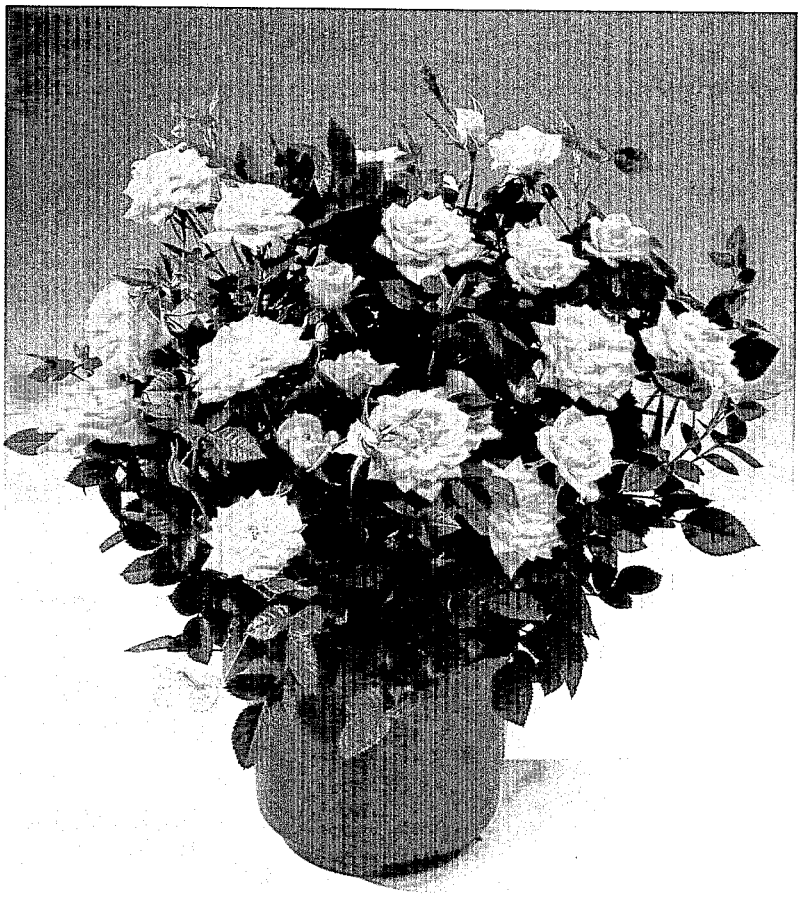

UNITED STATES PATENT AND TRADEMARK OFFICE

CERTIFICATE OF CORRECTION

PATENT NO. : Plant 8,527

DATED : January 4, 1994

INVENTOR(S) : Gijsbert de Ruiter

It is certified that error appears in the above-indentified patent and that said Letters Patent is hereby corrected as shown below:

Column 2, lines 17,18, after "organs." delete "4 depicts the bud just prior to opening of the petals."

Signed and Sealed this

Second Day of May, 1995

*Attest:*

Bruce Lehman

BRUCE LEHMAN

*Attesting Officer*

*Commissioner of Patents and Trademarks*